United States Patent [19]

Green

[11] Patent Number: 4,512,345
[45] Date of Patent: Apr. 23, 1985

[54] SURGICAL CLIP APPLYING APPARATUS, AND CLIPS AND CLIP TRAIN FOR USE THEREIN

[75] Inventor: David T. Green, Norwalk, Conn.

[73] Assignee: United States Surgical Corporation, Norwalk, Conn.

[21] Appl. No.: 429,250

[22] Filed: Sep. 30, 1982

[51] Int. Cl.³ .................................. A61B 17/12
[52] U.S. Cl. .................................. 128/325; 128/346; 227/DIG. 1
[58] Field of Search ............... 128/322, 346, 325, 326, 128/337; 227/DIG. 1; 29/243.56; 72/410; 24/255 SL; 206/339, 340; 251/10

[56] References Cited

U.S. PATENT DOCUMENTS

| | | |
|---|---|---|
| 1,199,653 | 9/1916 | Bacolini . |
| 1,452,373 | 4/1923 | Gomez . |
| 2,090,831 | 8/1937 | Burkhardt ........................ 1/49.1 |
| 2,140,593 | 12/1938 | Pankonin ........................ 206/340 |
| 2,222,726 | 11/1940 | Sorenson ........................ 206/340 |
| 2,758,302 | 8/1956 | White ........................ 227/DIG. 1 X |
| 3,047,874 | 8/1962 | Kelsey ........................ 1/349 |
| 3,086,208 | 4/1963 | Eby ........................ 1/56 |
| 3,098,232 | 7/1963 | Brown ........................ 1/349 |
| 3,152,336 | 10/1964 | Brady ........................ 1/349 |
| 3,234,636 | 2/1966 | Brown ........................ 29/212 |
| 3,247,852 | 4/1966 | Schneider ........................ 128/346 |
| 3,323,208 | 6/1967 | Hurley ........................ 30/124 |
| 3,461,876 | 8/1969 | Miller ........................ 128/346 |
| 3,646,801 | 3/1972 | Caroli ........................ 72/410 |
| 3,653,389 | 4/1972 | Shannon ........................ 227/DIG. 1 B X |
| 3,899,914 | 8/1975 | Akiyama ........................ 72/410 |
| 3,924,629 | 12/1975 | Akiyama ........................ 128/325 |
| 3,958,576 | 5/1976 | Komiya ........................ 128/346 |
| 4,152,920 | 5/1979 | Green ........................ 72/410 |
| 4,212,303 | 7/1980 | Nolan ........................ 128/346 |
| 4,226,242 | 10/1980 | Jarvik ........................ 128/325 |
| 4,246,903 | 1/1981 | Larkin ........................ 128/325 |
| 4,275,813 | 6/1981 | Noiles ........................ 227/DIG. 1 X |
| 4,296,751 | 10/1981 | Blake et al. ........................ 128/325 |
| 4,316,468 | 2/1982 | Klieman et al. ........................ 128/325 |
| 4,325,376 | 4/1982 | Klieman et al. ........................ 128/325 |
| 4,361,229 | 11/1982 | Mericle ........................ 206/339 |
| 4,380,238 | 4/1983 | Colucci et al. ........................ 128/346 |

FOREIGN PATENT DOCUMENTS

| | | | |
|---|---|---|---|
| 2525650 | 12/1976 | Fed. Rep. of Germany | 128/346 |
| 713384 | 8/1954 | United Kingdom | 128/337 |
| 1335672 | 10/1973 | United Kingdom | 128/346 |
| 2088723 | 6/1982 | United Kingdom | 128/325 |

*Primary Examiner*—Michael H. Thaler
*Attorney, Agent, or Firm*—Robert R. Jackson; John E. Nathan

[57] ABSTRACT

Surgical clip applying apparatus operable entirely by one hand for advancing clips one at a time into a pair of jaws which close the clip on body tissue. The clips are fed to the jaws in a line. The clips releasably intercouple with one another to form a train which is advanced by a clip pusher acting on the distal-most clip in the train. As the distal-most clip enters the jaws, it is uncoupled from the clip train, and the jaws then close the clip. The pusher is then retracted behind the next clip in the train to ready the apparatus for another cycle of operation.

19 Claims, 24 Drawing Figures

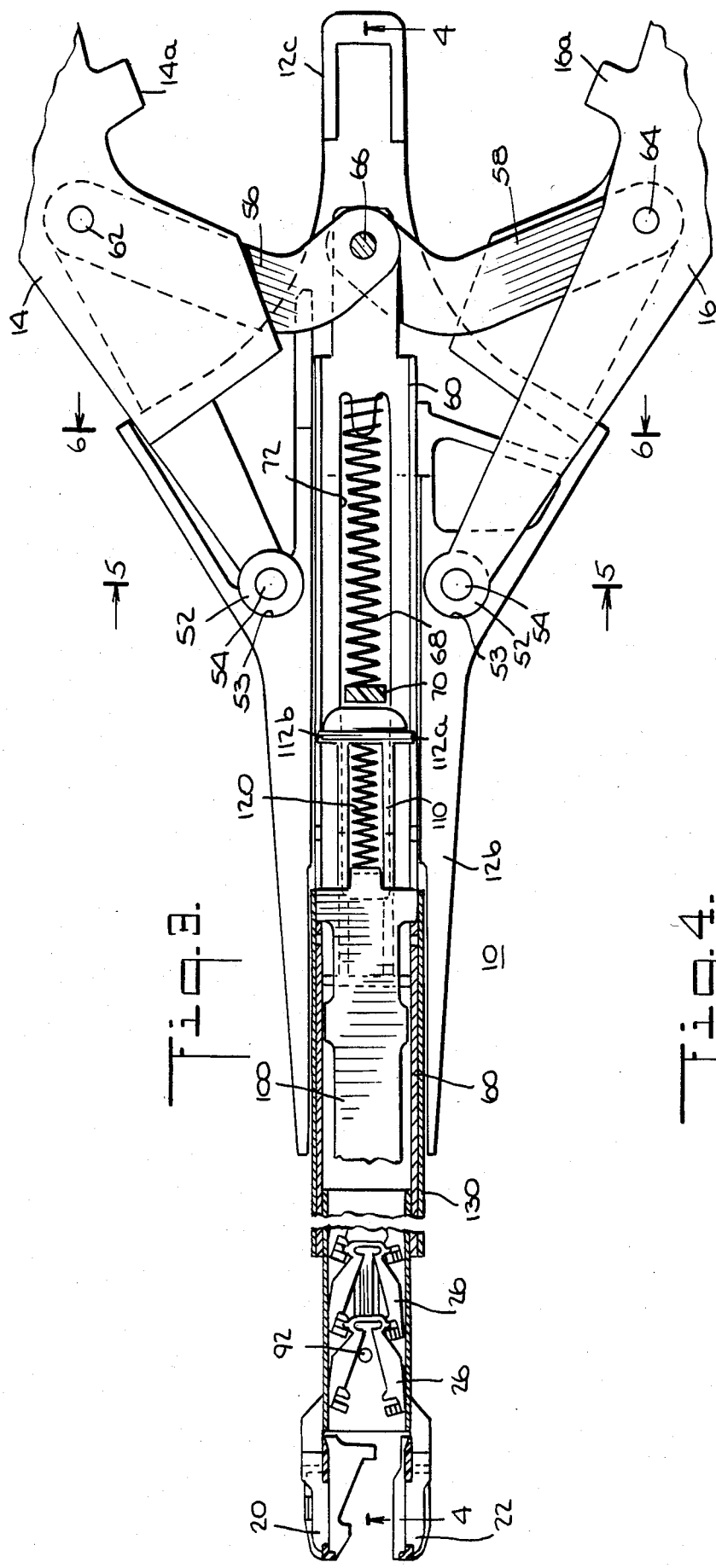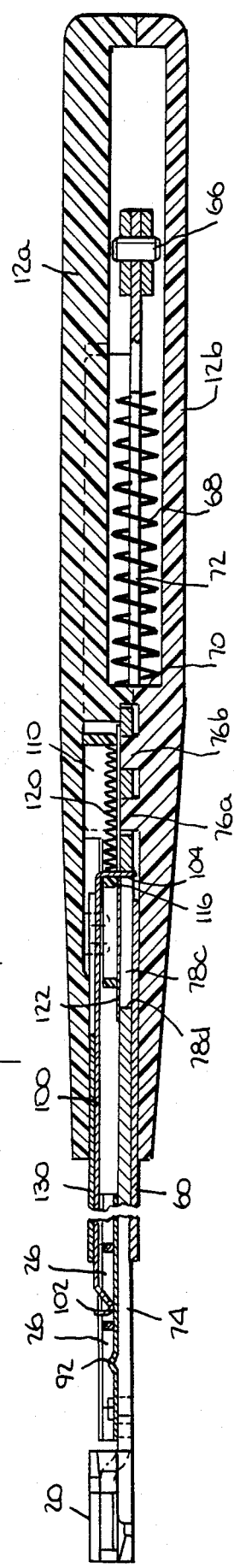
Fig. 3.
Fig. 4.

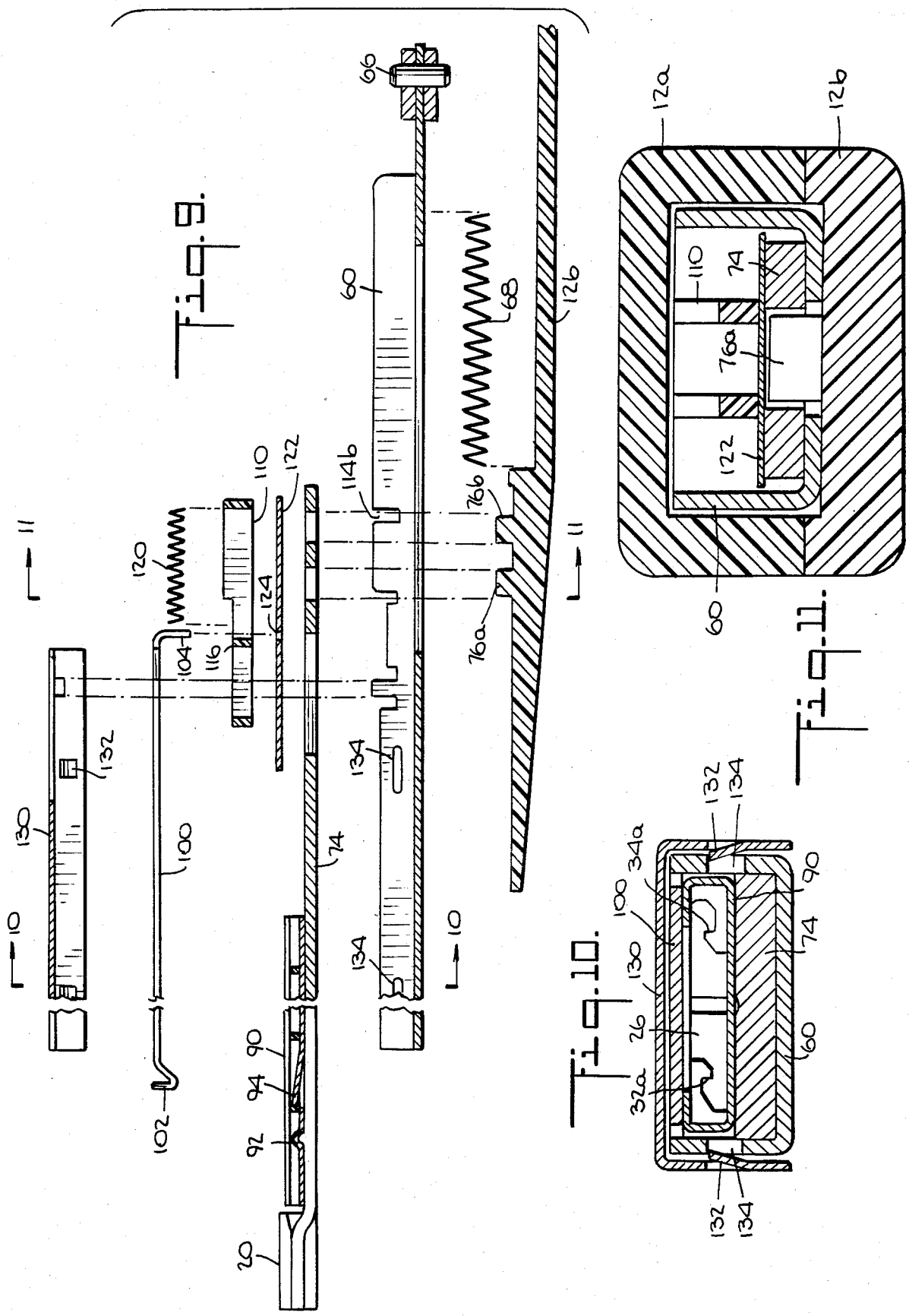

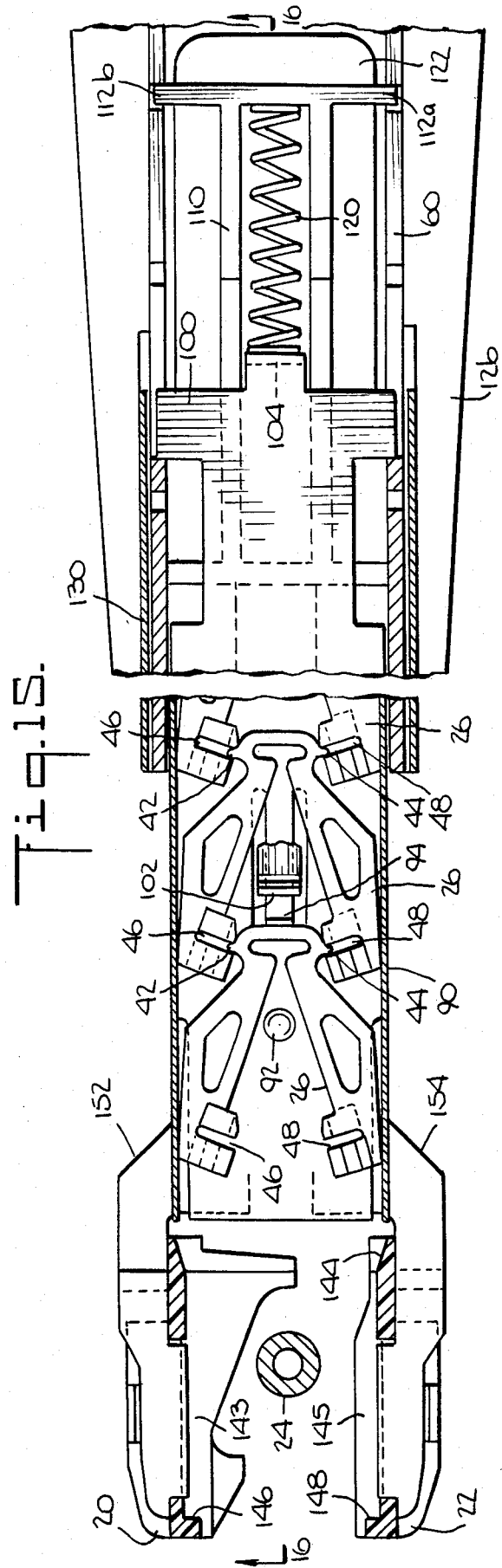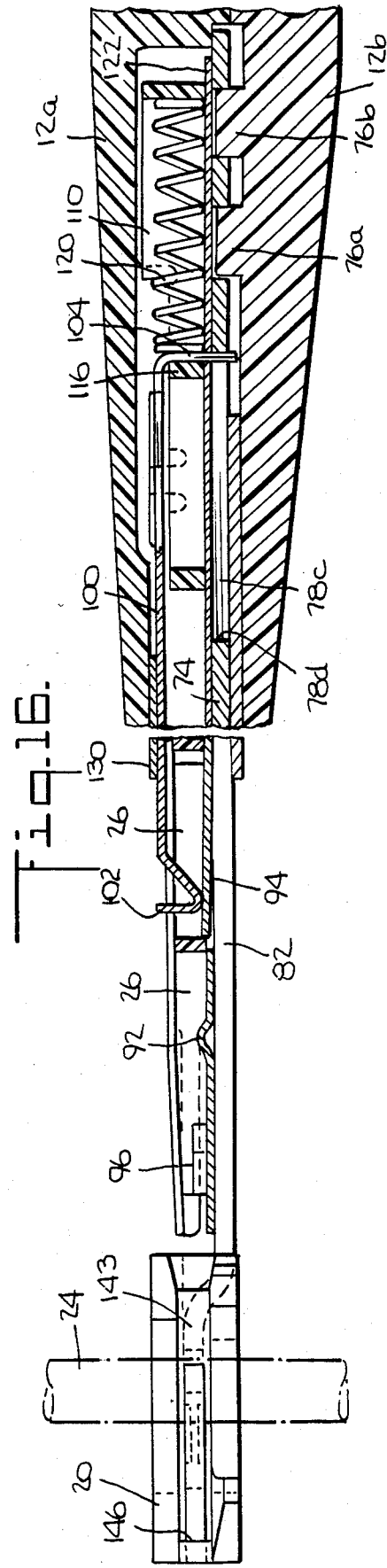

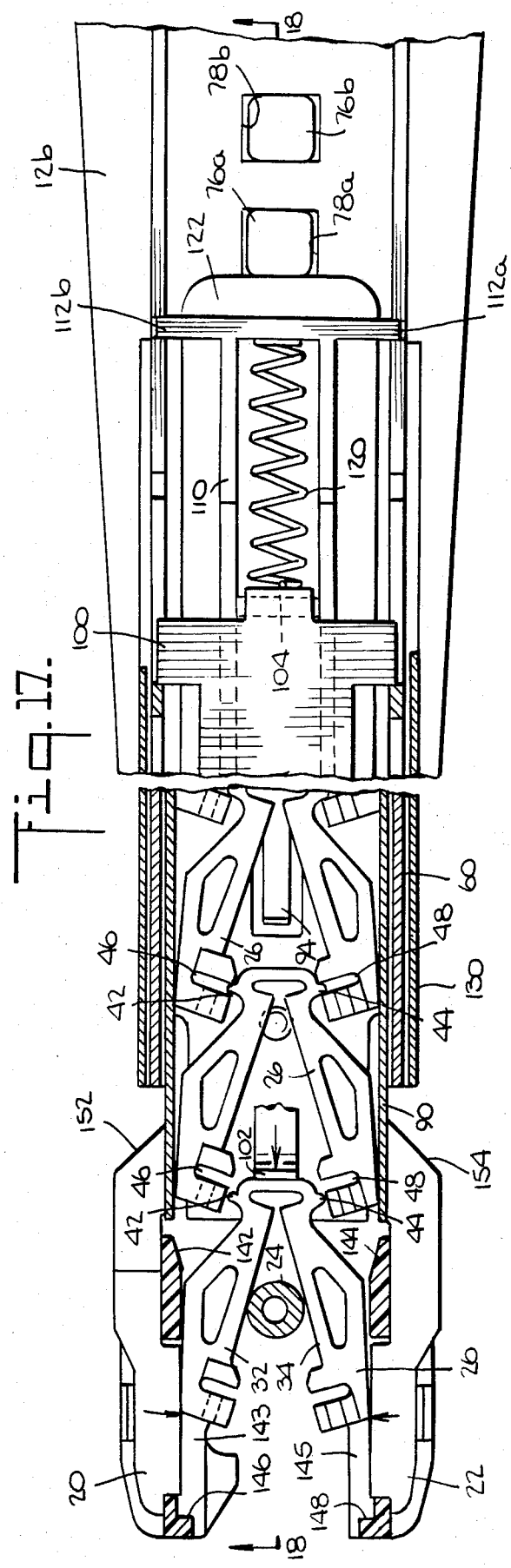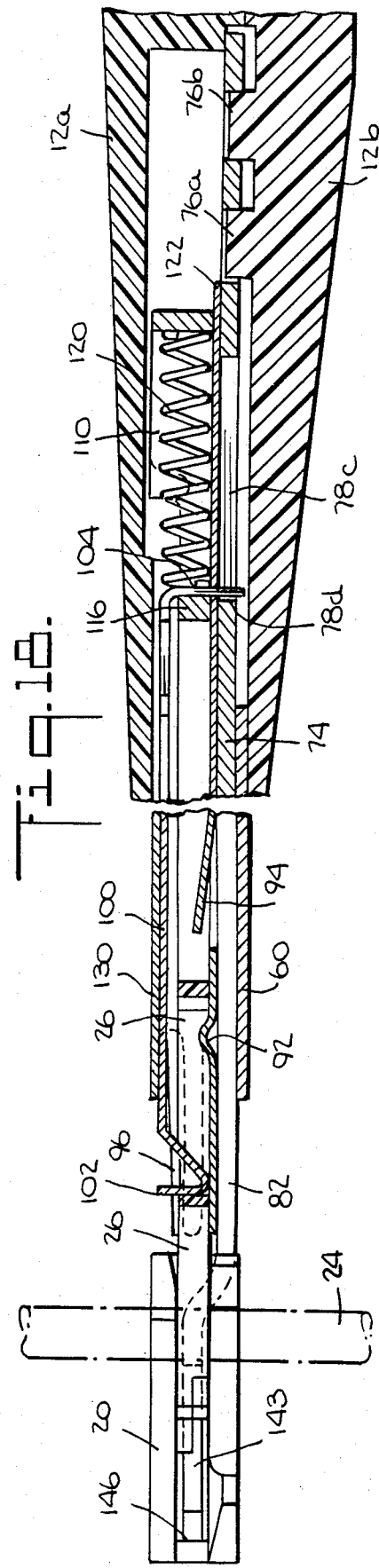

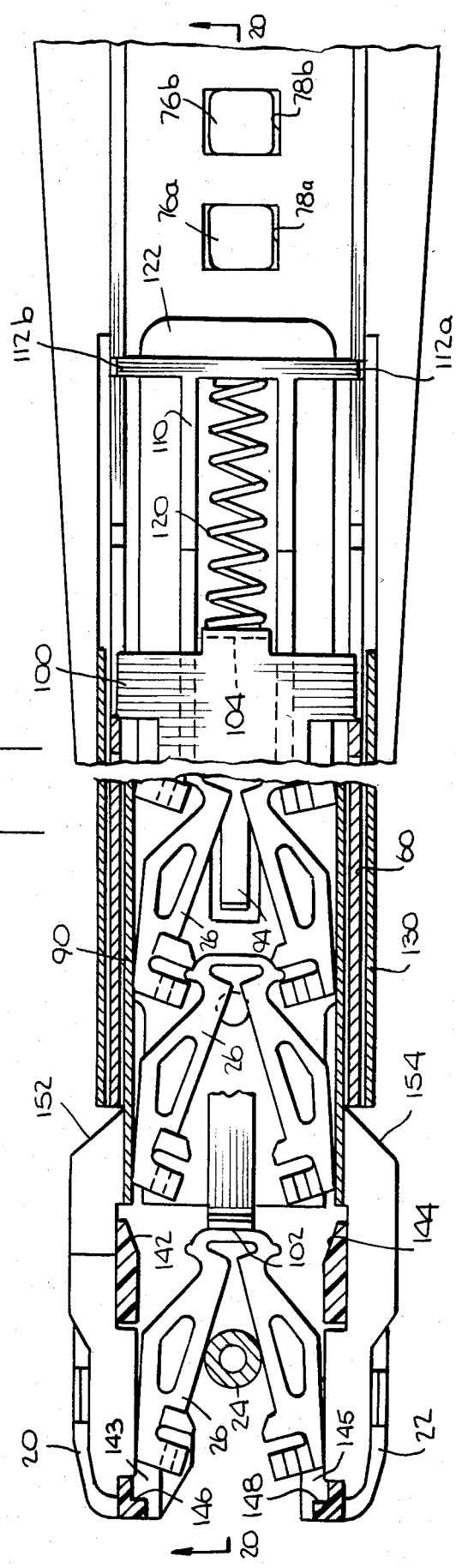
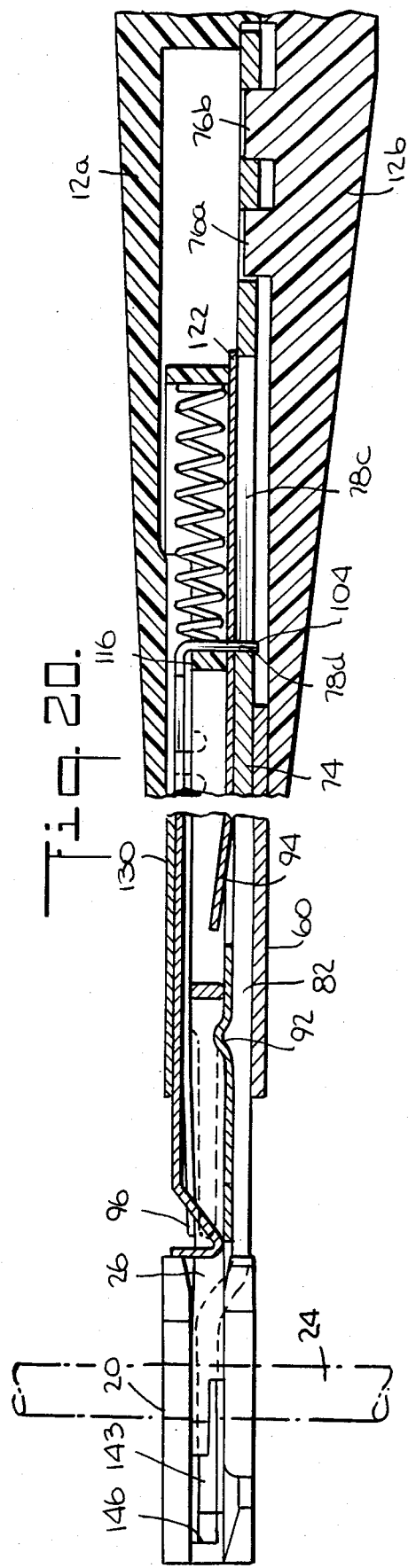

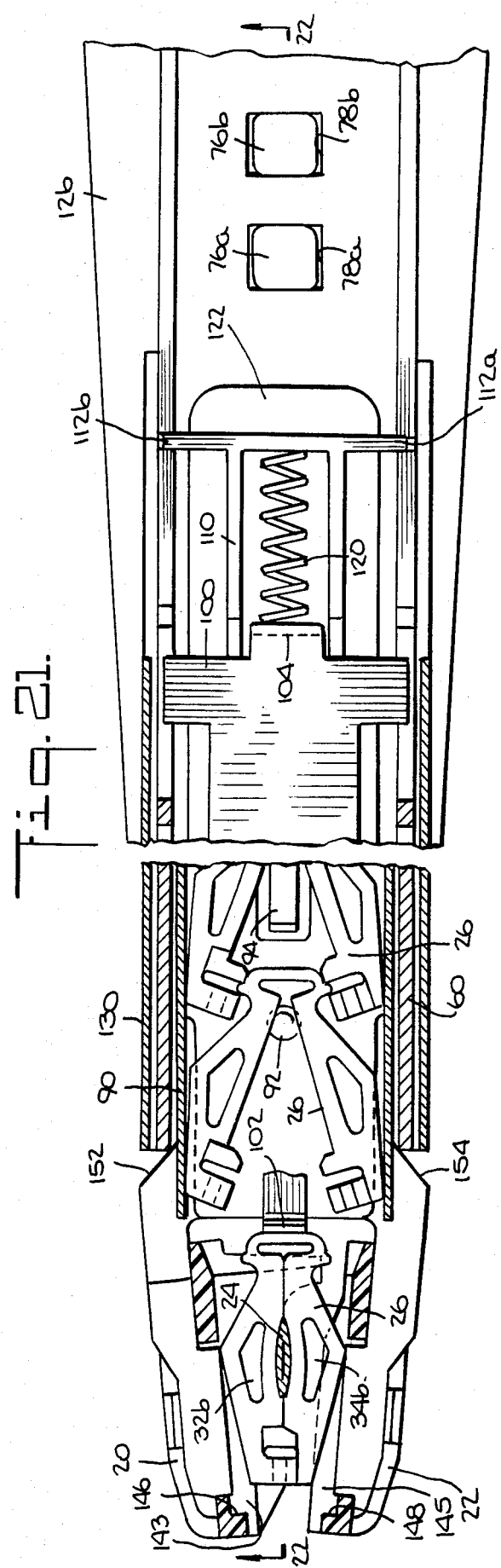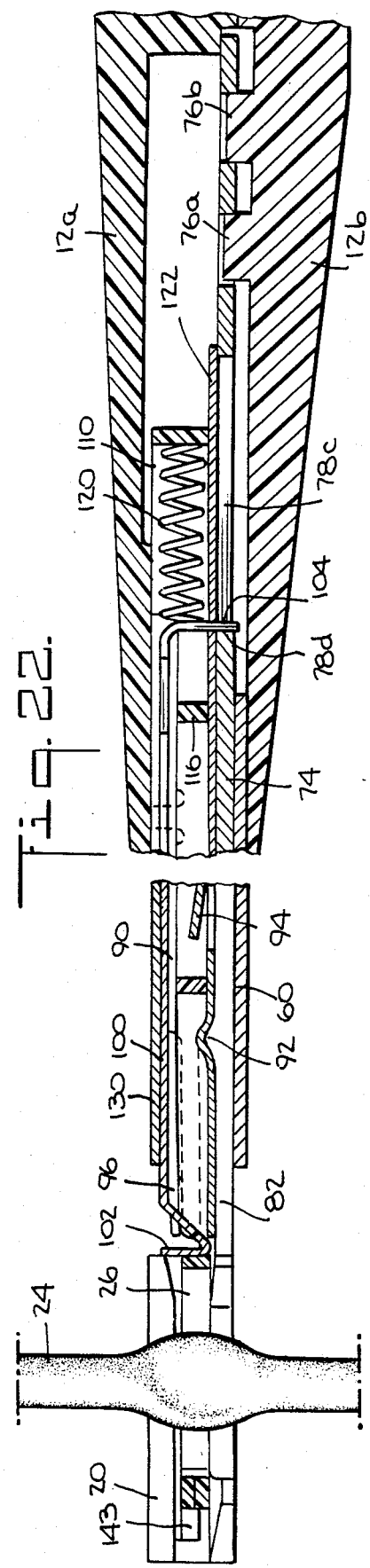

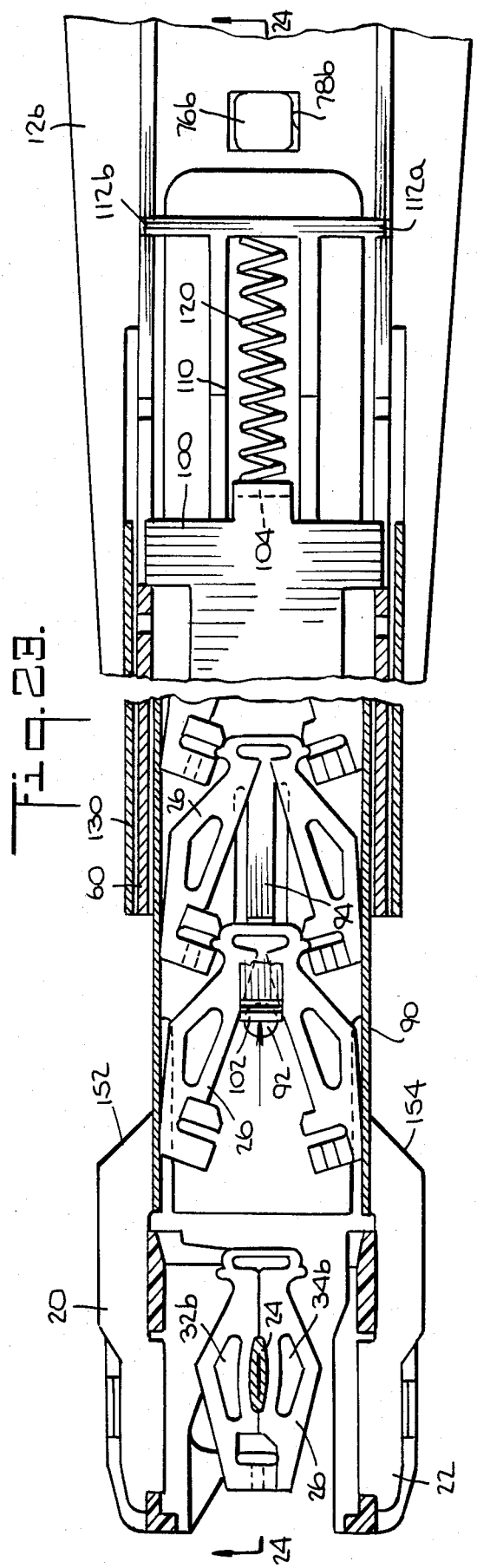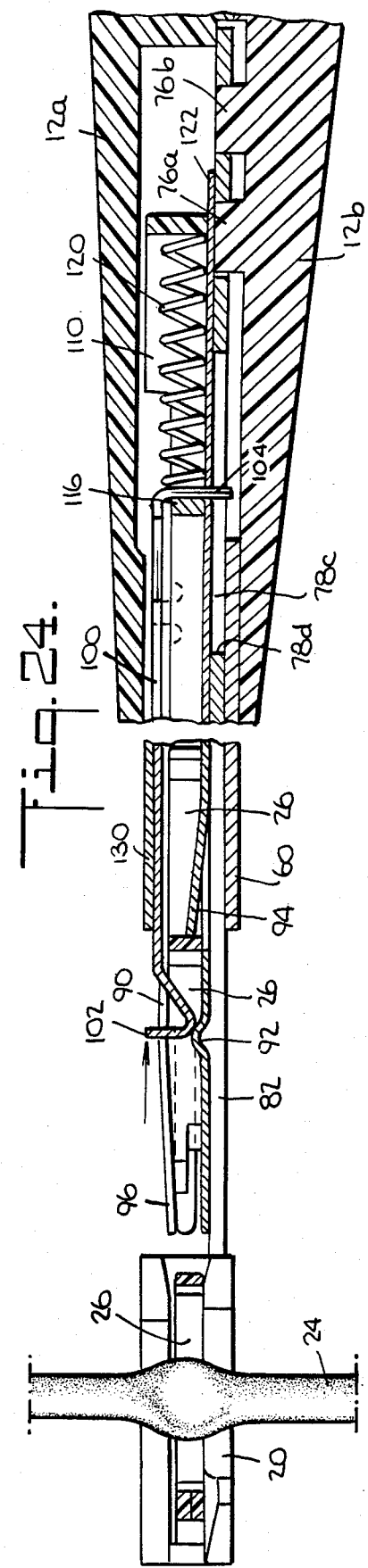
Fig. 23.
Fig. 24.

SURGICAL CLIP APPLYING APPARATUS, AND CLIPS AND CLIP TRAIN FOR USE THEREIN

BACKGROUND OF THE INVENTION

This invention relates to hemostatic surgical clip applying methods and apparatus, and to surgical clips for use therein. More particularly, the invention relates to hemostatic surgical clip applying methods and apparatus in which clips contained in a clip applying instrument are automatically fed one at a time to the clip closing portion of the instrument as the instrument is operated.

In-line feeding of the clips in surgical clip applying apparatus is highly desirable because it eliminates the need for a bulky clip magazine near the distal end of the instrument. Such a magazine may obstruct the surgeon's view of the jaws of the instrument when the instrument is being used to apply hemostatic clips to body tissue in a surgical procedure. Several techniques for in-line surgical clip feeding have been developed, but many of these techniques tend to be relatively complicated and to require a large number of parts or elements to advance the clips to the clip closing portion of the apparatus.

It is therefore an object of this invention to improve and simplify surgical clip applying methods and apparatus.

It is a more particular object of this invention to provide surgical clip applying methods and apparatus with improved and simplified in-line feeding of the clips to the clip closing portion of the apparatus.

SUMMARY OF THE INVENTION

These and other objects of the invention are accomplished in accordance with the principles of the invention by providing surgical clips which releasably couple together to form a linear array or train. The clip train is slidably disposed along the longitudinal axis of a clip applying instrument. A pusher, reciprocally mounted in the clip applying instrument, contacts the forwardmost clip in the train and pushes it in the distal direction toward the clip closing jaws of the instrument. The remaining clips in the train are pulled along with the forwardmost clip until, as the forwardmost clip is entering the jaws, that clip is uncoupled from the remaining clips in the train and seated in the jaws. The jaws then operate to close the clip around the body tissue to be clipped. When the pusher is subsequently released, the jaws release the closed clip. The pusher also retracts to the proximal side of the next clip, which is now the forwardmost clip in the clip train. The instrument is ready to repeat its operating cycle.

Although the clips may be made of biologically acceptable metal, they are preferably made of biologically acceptable plastic, most preferably of biologically absorbable plastic material. Plastic clips may be preferred because, if left in the body after the surgical procedure, they do not degrade the quality of subsequent radiographs (X-rays) the way metal clips may. Biologically absorbable plastic clips have the further advantage that they are absorbed by the body after the clipped tissue has healed. Possibly undesirable migration of the clips in the body during the months and years following surgery is thereby avoided. If the clips are made of plastic (whether biologically absorbable or not), the normally free end portions of the arms of each clip preferably have mutually interlocking elements for holding the arms of the clip together after it has been closed as described above.

Further features of the invention, its nature and various advantages will be more apparent from the accompanying drawing and the following detailed description of the invention.

BRIEF DESCRIPTION OF THE DRAWING

FIG. 3 is a view similar to FIG. 2 but with several elements cut away to reveal additional interior elements.

FIGS. 5 and 6 are cross sectional views respectively taken along the lines 5—5 and 6—6 in FIG. 3.

FIG. 8 is a further exploded perspective view of a portion of the apparatus of FIG. 7.

FIG. 9 is an exploded elevational view of the apparatus of FIG. 8.

FIGS. 10 and 11 are cross sectional views respectively taken along the lines 10—10 and 11—11 in FIG. 9.

FIG. 12 is an enlarged plan view of an illustrative surgical clip for use in the apparatus of FIGS. 1-11.

FIG. 13 is a perspective view of the clip of FIG. 12 in position to be applied to body tissue. The clip applying apparatus which surrounds the clip during application of the clip to body tissue is not shown in FIG. 13 in order to show the clip itself most clearly.

FIG. 14 is a view similar to FIG. 13 but showing the clip applied to the body tissue.

FIGS. 15, 17, 19, 21, and 23 are a series of views similar to a portion of FIG. 3 depicting the operating sequence of the apparatus.

FIGS. 16, 18, 20, 22, and 24 are sectional views respectively taken along the lines 16—16, 18—18, 20—20, 22—22, and 24—24 in FIGS. 15, 17, 19, 21, and 23.

DETAILED DESCRIPTION OF THE INVENTION

Figure 1:
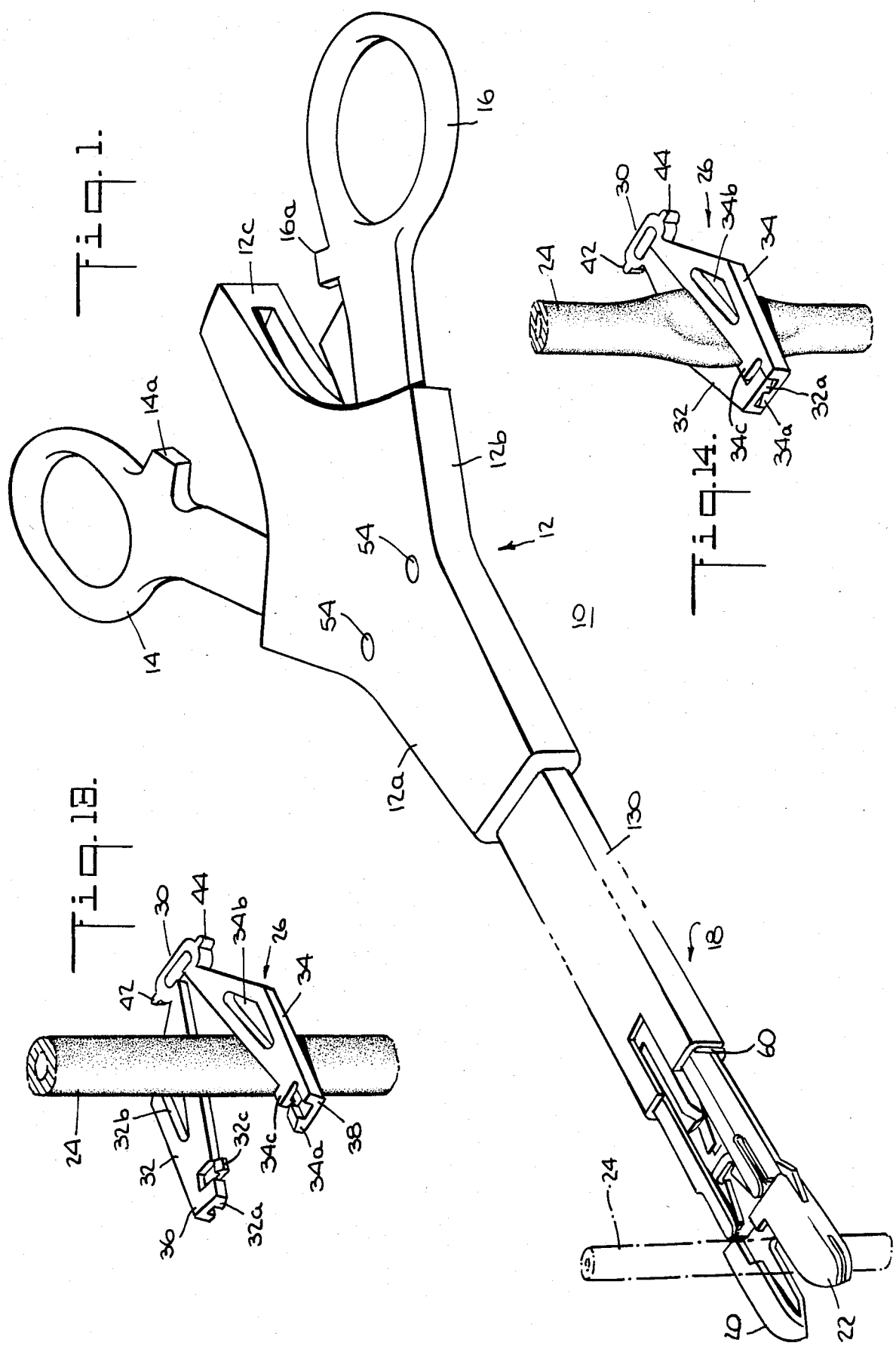
FIG. 1 is a perspective view of an illustrative embodiment of the surgical clip applying apparatus of this invention.
Figure 7:
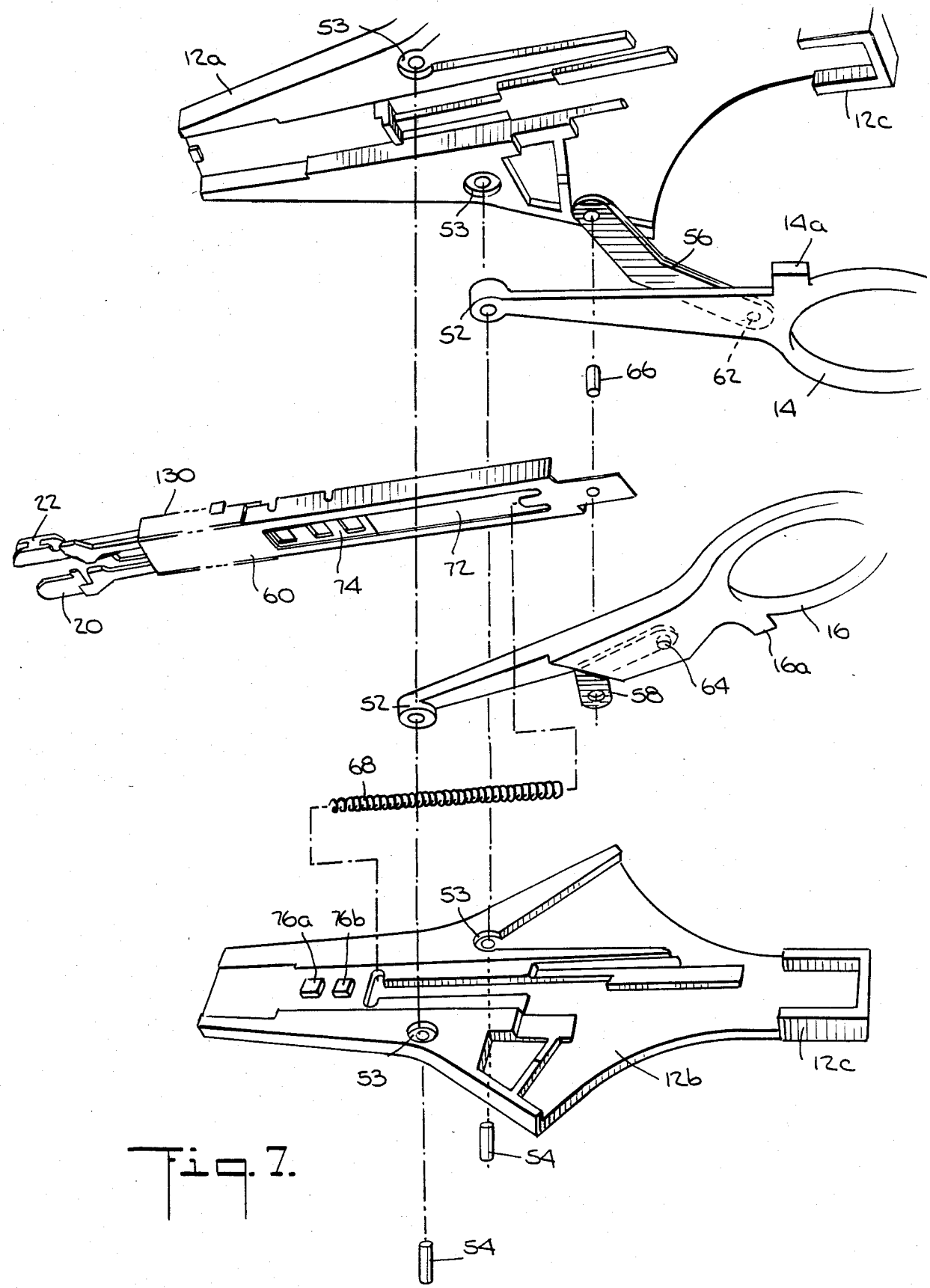
FIG. 7 is a partly exploded perspective view of the apparatus of FIGS. 1-6.

As shown in FIG. 1, an illustrative embodiment of the clip applying apparatus 10 of this invention includes main body 12 in which two ring handles 14 and 16 are pivotally mounted to project out of the rearward or proximal end of the main body. Ring handles 14 and 16 are designed to receive, respectively, the thumb and a finger of one hand of the operator of the instrument. Instrument 10 is therefore operable entirely by one hand like a pair of scissors. Main body 12 is made up of two parts 12a and 12b (see FIG. 7) which may be held together in any conventional manner such as by a suitable adhesive.

A longitudinal shaft assembly 18 is mounted on body 12 and extends in the forward or distal direction from the body. Shaft assembly 18 terminates at the distal end of the apparatus in a pair of jaws 20, 22. In the operation of the instrument, jaws 20 and 22 are placed around the body tissue (e.g., blood vessel 24) to be clipped. Ring handles 14 and 16 are then squeezed together by the operator. This causes a clip 26 (FIG. 13) to be advanced along shaft assembly 18 and positioned in jaws 20, 22 with one arm of the clip in each jaw. Continued squeezing of the ring handles causes an outer sleeve portion of shaft assembly 18 to move distally relative to jaws 20, 22 and to thereby squeeze the jaws together. This closes the clip on the body tissue. When ring handles 14, 16 are subsequently released, jaws 20, 22 reopen and release the clipped tissue as shown in FIG. 14. The instrument is now ready to begin another cycle of operation.

Although it will be apparent to those skilled in the art that clips of other materials such as metal can be employed, the illustrative embodiment will be described for the most part in the context of the application of plastic clips.

An illustrative surgical clip 26 is shown in FIGS. 12-14, and a train of such clips is visible, for example, in FIG. 15. Each clip includes a base 30 and two arms 32, 34 extending from respective opposite ends of the base. The base and arms of the clip lie in a common plane. The clips are made so that the normally free end portions 36, 38 of the arms are resiliently biased apart, as shown for example in FIG. 12. The outer periphery of the base portion of each clip includes two laterally extending lugs 42, 44, each of which is adjacent a respective end of base 30. Alternatively, lugs 42, 44 could be respectively located along arms 32, 34. The inner periphery of the normally free end portion 36, 38 of each arm includes a slot 46, 48, respectively. When the physically separate and individual clips are associated with one another in a train, as shown for example in FIG. 15, the lugs 42, 44 of each clip are respectively releasably received in and engaged by the slots 46, 48 in the immediately following clip. The arms of each clip are prevented from spreading farther apart by the surrounding structure of the instrument. Accordingly, when the forwardmost clip in the train is pushed in the distal direction as described in detail below, all the succeeding clips in the train are pulled along at the same time.

The normally free end portions 36, 38 of the arms of each clip also include complementary latching elements 32a and 32c on arm 32 and 34a and 34c on arm 34. When the arms of the clip are squeezed together as shown in FIG. 14, latching elements 32a and 34a overlap and interlock with one another, and latching elements 32c and 34c similarly overlap and interlock with one another. Once these latching elements interlock, they hold the clip closed. The sense or direction of the overlap of latching elements 32a and 34a is opposite to the sense or direction of the overlap of latching elements 32c and 34c. For example, when clip 26 is viewed from above as in FIG. 14, latching element 32a is above latching element 34a, but latching element 32c is below latching element 34c. This makes the clip highly resistant to inadvertent reopening by helping to keep arms 32 and 34 co-planar.

Figure 2:
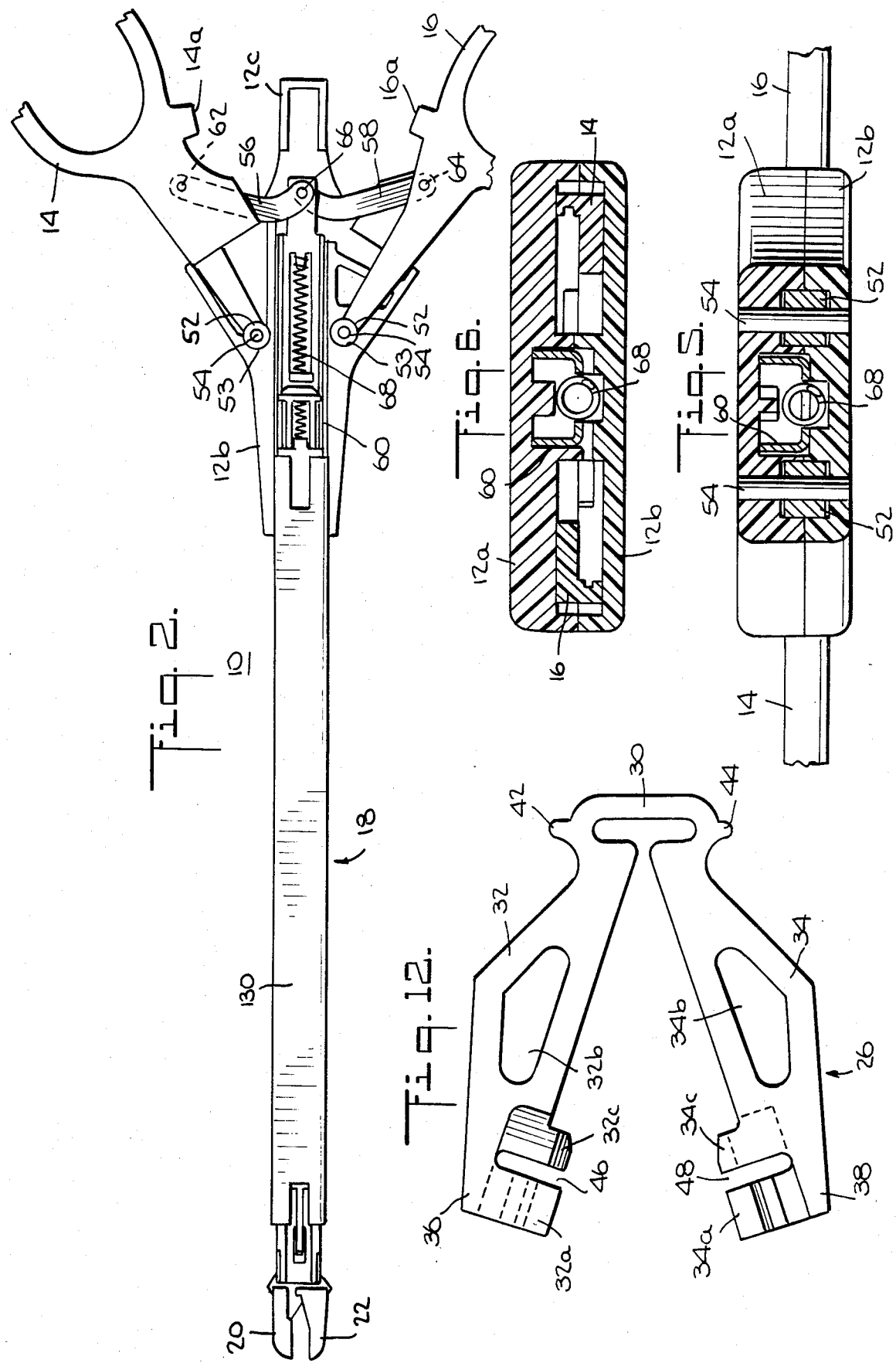
FIG. 2 is a top plan view of the apparatus of FIG. 1 with some of the upper parts removed to reveal some of the interior elements.

Considering now the construction of instrument 10 in more detail with reference to FIGS. 2 and 3, handles 14 and 16 are pivotally mounted on main body 12 by means of a substantially cylindrical knob 52 at the distal end of each ring handle, in cooperation with cylindrical sockets 53 in the interior of main body 12. If desired, a pin or screw 54 may be located coaxially in each of the above-described pivotal connections so as to extend through main body 12 and the associated knob 52 to help maintain handles 14 and 16 in main body 12. Pivotally mounted links 56 and 58 are connected between handles 14 and 16, respectively, and the proximal end of sleeve 60. Link 56 is pivotally connected to handle 14 by pin 62; link 58 is pivotally connected to handle 16 by pin 64; and both links are pivotally connected to sleeve 60 by pin 66. Sleeve 60 is mounted for longitudinal reciprocal motion relative to housing 12. When handles 14 and 16 are squeezed together, links 56 and 58 drive sleeve 60 in the distal direction.

Figure 4:
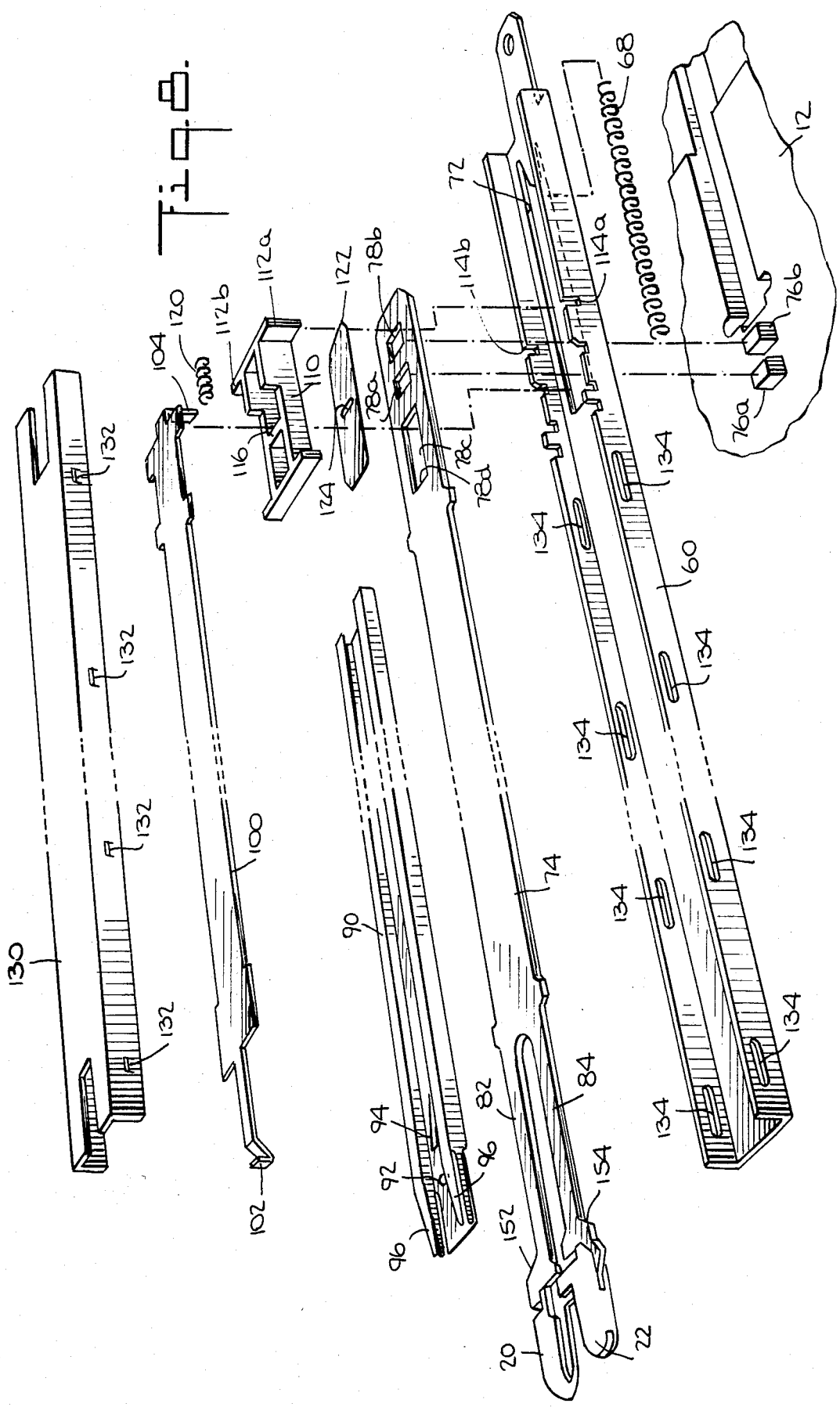
FIG. 4 is an elevational sectional view taken along the line 4—4 in FIG. 3.

Sleeve 60 is resiliently biased in the proximal direction by compression coil spring 68, which is compressed between surface 70 (FIGS. 3 and 4) inside housing 12 and the proximal end of aperture 72 in sleeve 60. The proximal resilient bias of sleeve 60 also resiliently biases handles 14 and 16 apart. The outward motion of handles 14 and 16 is stopped by contact of the handle shafts with the sides of main body housing 12 as shown in FIG. 3. Spring 68 is thus the main return spring of the instrument.

As is best seen in FIG. 8, sleeve 60 is basically a channel-shaped member, preferably made of metal. Inside the channel defined by sleeve 60 is jaw member 74, which is fixedly mounted relative to housing 12 by cooperation of housing lugs 76a and 76b with apertures 78a and 78b in the proximal end portion of jaw member 74. Lugs 76 pass freely through the distal portion of aperture 72 in sleeve 60. The distal end portion of jaw member 74 is bifurcated to define two spaced, substantially parallel arms 82 and 84. Jaws 20 and 22 are respectively mounted on the distal ends of arms 82 and 84. Jaw member 74 is preferably made of resilient metal so that arms 82 and 84 can be deflected toward one another as described in detail below, and so that when the force on them is released, they will resume their original spacing.

Fixedly mounted on the upper surface of jaw member 74 is clip train container 90. As best seen in FIG. 10, clip train container 90 is a C-shaped channel member whose longitudinal axis is aligned with the longitudinal axis of jaw member 74. The channel of clip train container 90 contains a plurality of clips 26 arranged in an interlocking linear array or train as described in detail above (see again FIG. 15). The normally free ends 36, 38 of each clip point in the distal direction, and the train of clips is aligned with the longitudinal axis of clip train container 90. Clip train container 90 has a raised dimple or detent 92 near the distal end of the channel which helps to uncouple the distal-most clip from the clip train as described in detail below. Clip train container 90 also has a leaf spring portion 94 which projects up into the channel and which acts as a pawl member to substantially prevent the clip train from moving in the proximal direction. Clips can move past pawl spring 94 in the distal direction by depressing the pawl spring as they pass. However, clips can not move back in the proximal direction because the distal end of pawl spring 94 will contact the base 30 of a clip approaching the spring from the distal side and prevent further proximal motion of the clip (see FIGS. 23 and 24). The clips are prevented from inadvertently falling out of the distal end of container 90 by inwardly biased leaf spring elements 96 (FIG. 8) near the distal end of container 90.

As best seen in FIG. 8, the upper portion of clip train container 90 is open to permit pusher finger 102 at the distal end of pusher member 100 to extend down into container 90 and to contact the base 30 of the distal-most clip in container 90. Pusher member 100 is mounted over clip train container 90 for longitudinal reciprocal motion relative thereto. Pusher member 100 is coupled to channel member 60 by means of coupler 110 and compression coil spring 120. Coupler 110 fits in a proximal portion of channel 60 and includes a pair of laterally extending lugs 112a and 112b which respectively fit in slots 114a and 114b in channel member 60 so that coupler 110 reciprocates longitudinally with channel member 60. The proximal end of pusher member 100 includes downwardly extending finger 104, which fits into coupler 110 on the proximal side of transverse bar 116 in the coupler. Finger 104 is resiliently biased in the distal direction against transverse bar 116 by compression coil spring 120, which also fits in coupler 110 and acts between the proximal end of the coupler and finger 104. Spring guard 122 below coupler 110 keeps spring 120 in coupler 110. Aperture 124 in spring guard 122 allows the extreme lower end of finger 104 on pusher member 100 to enter aperture 78c in jaw member 74 (see FIG. 4).

The above-described coupling between pusher member 100 and channel member 60 operates as follows: As channel member 60 moves in the distal direction in response to operation of handles 14 and 16, coupler 110 and spring 120 cause pusher member 100 to move with channel member 60 until finger 104 contacts the distal end 78d of aperture 78c in jaw member 74. Thereafter, further distal motion of pusher member 100 is prevented by this contact between finger 104 and surface 78d. Channel member 60 can continue to move in the distal direction, but pusher member 100 is stopped. Spring 120 compresses to permit this differential motion of elements 60 and 100. When handles 14 and 16 are released, channel member 60 moves back in the proximal direction and pusher member 100 is pulled back with member 60 by contact of transverse bar 116 with finger 104.

Shaft assembly 18 is covered by cover 130 (FIG. 8) which is secured to channel member 60 by cooperation of tongues 132 on cover 130 and apertures 134 on channel member 60 (see FIG. 10).

The sequence of operation of the apparatus in response to squeezing and then releasing handles 14 and 16 is best seen in FIGS. 15-24. FIGS. 15 and 16 show the apparatus before squeezing of the handles begins. Channel member 60, coupler 110, and pusher member 100 are all in their proximal-most positions. Pusher finger 102 is on the proximal side of the distal-most clip 26 in the clip train. Jaws 20 and 22 are open and positioned around the body tissue 24 to be clipped.

In FIGS. 17 and 18, squeezing of handles 14 and 16 has begun. Accordingly, channel member 60 has moved in the distal direction, carrying with it coupler 110 and pusher member 100. Pusher finger 102 has contacted the base 30 of the distal-most clip 26 in the clip train, thereby advancing that clip and all the other clips in the distal direction. When the apparatus reaches the stage shown in FIGS. 17 and 18, the distal-most clip has passed detent 92, is nearly out of clip train container 90, and has begun to enter jaws 20 and 22 with one arm of the clip on each side of the body tissue 24 to be clipped. Jaws 20 and 22 have longitudinal slots 143 and 145, respectively, for receiving the arms of the clip to thereby maintain the proper location and orientation of the clip. Also, as the distal-most clip is entering the jaws, outer peripheral portions of clip arms 32 and 34 respectively contact synclinal cam surfaces 142 and 144 on jaws 20 and 22. This causes the arms of the distal-most clip to pivot toward one another slightly, which brings lugs 42 and 44 on the distal-most clip together enough to uncouple the distal-most clip from the succeeding or next-to-distal-most clip in the clip train. At the same time, the next-to-distal-most clip contacts detent 92 which increases the resistance of the clip train to distal motion and thereby helps to uncouple the distal-most clip from the clip train. FIG. 17 shows the distal-most clip just after uncoupling from the clip train as described above. It should be noted that detent 92 is sized and positioned so that it retards the clip train only when the distal-most clip is to be uncoupled. At other positions of the clip train, detent 92 does not contact any portion of the train.

As a possible alternative to uncoupling the distal-most clip by squeezing the arms of that clip together, the distal-most clip could be uncoupled by allowing the arms of the next-to-distal-most clip to spread apart. This could be accomplished by spreading apart the side walls of clip train container 90 at the point at which uncoupling is desired.

FIGS. 19 and 20 show the apparatus after still further squeezing of handles 14 and 16. Elements 60, 110, and 100 have advanced still farther in the distal direction. Pusher finger 102 has now pushed distal-most clip 26 completely out of clip train container 90 and fully into jaws 20 and 22. The clip is prevented from falling out of the end of jaws 20 and 22 by inwardly projecting clip stops 146 and 148 near the distal ends of the jaws. The remaining clips in the clip train have remained stationary since the distal-most clip was uncoupled from the train as shown in FIG. 17 because the next-to-distal-most clip is captured between detent 92 and pawl spring element 94. The distal end of channel member 60 is just about to contact diverging cam surfaces 152 and 154 on jaws 20 and 22 respectively. Also, the lower end of finger 104 on pusher member 100 has just contacted the distal end 78d of aperture 78c in jaw member 74. This prevents further distal motion of pusher member 100 as squeezing of handles 14 and 16 continues.

The condition of the apparatus in response to the final portion of the squeezing of handles 14 and 16 is shown in FIGS. 21 and 22. Elements 60 and 110 continue to move in the distal direction, but pusher member 100 is prevented from such further distal motion by contact of finger 104 with surface 78d. Accordingly, no further distal motion of the distal-most clip occurs. The distal end of channel member 60 engages cam surfaces 152 and 154 on jaw member 74 and cooperates with those surfaces to squeeze jaws 20 and 22 toward one another. This squeezes the arms of the distal-most clip together until clip elements 32a, 32c, 34a, and 34c interlock to hold the clip closed around body tissue 24. The arms of the clip may include apertures 32b and 34b, respectively, to provide some relief of the pressure on the tissue. However, the clip preferably applies sufficient pressure to the tissue to produce hemostasis without causing undue tissue damage.

The clip-applying stroke of the instrument is now complete. Handles 14 and 16 can not be squeezed together any farther because handle stops 14a and 16a (FIGS. 1-3) have contacted proximal projection 12c of main body 12. When the operator releases the squeezing pressure on handles 14 and 16, main return spring 68 drives channel member 60 back in the proximal direction. This allows jaws 20 and 22 to open and release the closed clip as shown in FIGS. 23 and 24. It also pulls pusher member 100 back so that pusher finger 102 rides up over the base 30 of what is now the distal-most clip in clip train container 90. The clip train is prevented from moving in the proximal direction by pawl spring element 94 in the bottom of clip train container 90.

When handles 14 and 16 have been fully released, the apparatus has returned to the condition shown in FIGS. 15 and 16 and is ready to begin another cycle of operation. Thus pusher finger 102 is limited to motion between (1) a proximal-most position in which the pusher finger is between the distal-most clip and the next-to-distal-most clip in the clip train at the location at which the clip train was left when the previously distal-most clip was uncoupled from the train, and (2) a distal-most position in which the distal-most clip has been fully pushed into jaws 20 and 22. The proximal-most position of pusher finger 102 is established by contact of ring handles 14 and 16 with main body housing 12 as shown in FIG. 3. The distal-most position of pusher finger 102 is established by contact between finger 104 and surface 78d. In this way one, and only one, clip is pushed into jaws 20 and 22 during each operating cycle of the apparatus.

Clips 26 may have various sizes depending on their intended use. Typical clips may be about 10 mm long and 8 mm wide before being closed. Much smaller clips may be used for certain applications in microsurgery. Larger clips may be used for other purposes such as closing vas deferens and oviducts. The clip applying apparatus is sized appropriately for the clips it is to apply.

As mentioned above, clips 26 may be either metal or plastic, and may be either biologically absorbable or nonabsorbable. Preferred absorbable polymers include homopolymers and copolymers of glycolide, lactide and p-dioxanone. Preferred nonabsorbable polymers include nylon, polyester, and polypropylene. Typical metals include aluminum, magnesium, stainless steel, tantalum, and various alloys of these materials, some of which may also be biologically absorbable.

The provision of apparatus which advances a clip train by pushing on the distal-most staple in the train greatly facilitates use of plastic clips because it avoids the problems associated with attempting to push a line of plastic clips from the rear. If pushed from the rear, a line of such clips may tend to buckle and therefore bind in the apparatus. Also, because of the nature of the plastic clip material, the line of clips may foreshorten when pushed from the rear, thereby making it difficult or impossible to maintain the clips in registration with the surrounding apparatus for proper progression of one clip into the jaws during each operating cycle of the appratus.

Advantageously, the entire apparatus can be made economically disposable after use in a single surgical procedure or after the supply of clips in clip train container 90 is exhausted. In this way all difficulty and expense associated with cleaning, sterilizing, and reloading the apparatus for reuse can be entirely avoided. Because channel member 60 acts as a reciprocating sleeve to close jaws 20 and 22, most of the operating elements in the apparatus must transmit only tension and compression forces, not bending moments as in instruments which operate like scissors or pliers. The instrument can therefore be made with an extremely light and slender construction. The relatively small amounts of material required, as well as the simplicity of the design of the instrument, make it economical to produce the instrument as a disposable item if desired. For this purpose, main body 12 and much of handles 14 and 16 can be made of inexpensive plastic materials. Alternatively, the apparatus can be made with a permanent and reusable construction if desired. In either case, the in-line feeding of the clips and the slender construction of shaft assembly 18 permit a clear view of the jaws at all times. This is highly desirable in delicate surgical procedures.

It is to be understood that the individual clips and/or clip train of this invention are usable with clip applying instruments other than the particular one described above. For example, in my concurrently filed, commonly assigned, U.S. patent application Ser. No. 429,249 entitled "Surgical Clip Applying Apparatus Having Fixed Jaws", which is hereby incorporated by reference herein, clip applying apparatus is shown which has fixed jaws and which may use the clip train of this invention (see especially FIGS. 1-17 of that application). Other modifications of the particular embodiments shown and described herein are also within the scope and spirit of the invention. For example, other types of actuator elements, such as a pistol grip and trigger arrangement, could be substituted for ring handles 14 and 16 in the apparatus of FIGS. 1-24 herein.

I claim:

1. Surgical clips for use in a device for applying a succession of surgical clips to body tissue, each surgical clip comprising:

a base;

two arms, each arm being connected adjacent one of its ends to a respective end of the base, and the other ends of the arms being initially free and laterally spaced from one another, the longitudinal axes of the base and arms defining the plane of the clip, each arm having an inner surface which is opposite the inner surface of the other arm and an outer surface which is opposite the inner surface of the arm;

first coupling means comprising a member unitary with the clip and projecting from the outer surface of each arm remote from the initially free end of the arm, each projecting member having a longitudinal axis which is substantially perpendicular to the longitudinal axis of the associated arm and parallel to the plane of the clip; and second coupling means comprising a slot in the inner surface of each arm remote from the base for removably receiving an associated one of the projecting members of an adjacent clip so that a plurality of said clips can be intercoupled in a linear array in which each clip is pulled along by the preceding clip in the array when the preceding clip moves in a direction away from the clip.

2. The surgical clips defined in claim 1 wherein the clips are made of plastic material and wherein each clip further comprises means for causing the ends of the arms remote from the base to interlock with one another when the arms are squeezed together.

3. The apparatus defined in claim 2 wherein the clips are made of biologically absorbable material.

4. The apparatus defined in claim 2 wherein the means for causing the ends of the arms remote from the base to interlock with one another when the arms are squeezed together comprises first and second latching elements longitudinally spaced on each arm of the clip, and wherein each slot is formed by the space between the latching elements on the associated arm.

5. The apparatus defined in claim 4 wherein, when the arms of the clip are squeezed together, the first latching element on a first arm lies over the first latching element on the second arm and the second latching element on the first arm lies under the second latching element on the second arm.

6. The apparatus defined in claim 1 wherein the planes of all of the clips in the array are co-planar.

7. Apparatus for applying a plurality of surgical clips to body tissue one at a time in succession comprising:

a plurality of surgical clips in a linear array, each clip including (1) a base adjacent the succeeding clip, (2) two arms attached to opposite ends of the base and extending in the direction of the preceding clip, the ends of the arms remote from the base being resiliently biased apart, (3) first coupling means disposed on the inner surface of the arms, and (4) second coupling means disposed on the outer surface of the clip for releasably coupling the clip to the first coupling means of the succeeding clip in the array so that each clip pulls along the succeeding clip when advanced in the direction away from the succeeding clip;

third means disposed adjacent to, but just beyond, the forwardmost clip in the array for closing a clip pushed into the third means; and fourth means for sequentially engaging the forwardmost clip, pushing the forwardmost clip toward the third means, and deflecting the arms of the forwardmost clip toward one another to uncouple the forwardmost clip from the succeeding clip as the forwardmost clip enters the third means.

8. The apparatus defined in claim 7 further comprising:

means for limiting the motion of the portion of the fourth means which engages the forwardmost clip between (1) a rearwardmost position in which the portion of the fourth means which engages the forwardmost clip is between the forwardmost clip and the next-to-forwardmost clip in the array at the location of the array when the previously forwardmost clip was uncoupled from the array, and (2) a forwardmost position in which the forwardmost clip is fully pushed into the third means.

9. The apparatus defined in claim 8 further comprising means for releasably retaining the next-to-forwardmost clip in the array at its location when the previously forwardmost clip was uncoupled from the array.

10. The apparatus defined in claim 8 further comprising means for releasably retarding the forward motion of the next-to-forwardmost clip when the forwardmost clip is to be uncoupled.

11. The apparatus defined in claim 10 wherein the means for releasably retarding the forward motion of the next-to-forwardmost clip comprises detent means for contacting the next-to-forwardmost clip when the forwardmost clip is to be uncoupled.

12. The apparatus defined in claim 7 wherein the third means includes a pair of laterally spaced, relatively movable jaws for receiving and closing the forwardmost clip, and wherein the fourth means includes fifth means for actuating the third means to move the jaws toward one another after uncoupling the forwardmost clip from the succeeding clip.

13. The apparatus defined in claim 12 wherein the fifth means comprises:

cam surfaces mounted on the jaw members; and a sleeve member mounted for reciprocal motion toward and away from the jaws for engaging the cam surfaces and thereby moving the jaws toward one another when the sleeve member is reciprocated toward the jaws.

14. The apparatus defined in claim 7 wherein the longitudinal axes of the base and the arms of each clip define the plane of the clip, and the planes of all of the clips in the array are co-planar.

15. The apparatus defined in claim 14 wherein the fourth means comprises a pusher mounted for reciprocal motion toward and away from the base of the forwardmost clip for pushing the forwardmost clip toward the third means by pushing on the base of the forwardmost clip.

16. The apparatus defined in claim 15 wherein the fourth means further comprises sixth means for retracting the clip pusher from the forwardmost clip to a position preparatory to pushing on the base of the succeeding clip after the forwardmost clip has been closed.

17. The apparatus defined in claim 16 further comprising pawl means for substantially preventing the coupled clips from moving in the direction away from the third means.

18. The apparatus defined in claim 7 wherein the clips are made of plastic material and wherein the end portions of the arms remote from the base include means for causing the end portions of the arms to interlock when the clip is closed by the third means.

19. The apparatus defined in claim 18 wherein the clips are made of a biologically absorbable material.

* * * * *